(12) United States Patent
Flanders et al.

(10) Patent No.: US 9,526,790 B2
(45) Date of Patent: Dec. 27, 2016

(54) PHARMACEUTICAL AEROSOL COMPOSITIONS COMPRISING FLUTICASONE

(75) Inventors: Paul Flanders, Hatfield (GB); James Thompson, Hatfield (GB)

(73) Assignee: Generics [UK] Limited, Hertfordshire (GB)

( * ) Notice: Subject to any disclaimer, the term of this patent is extended or adjusted under 35 U.S.C. 154(b) by 418 days.

(21) Appl. No.: 12/666,001

(22) PCT Filed: Jun. 27, 2008

(86) PCT No.: PCT/GB2008/050518
§ 371 (c)(1),
(2), (4) Date: Oct. 14, 2010

(87) PCT Pub. No.: WO2009/001144
PCT Pub. Date: Dec. 31, 2008

(65) Prior Publication Data
US 2011/0020244 A1     Jan. 27, 2011

(30) Foreign Application Priority Data
Jun. 27, 2007 (GB) .................................. 0712454.8

(51) Int. Cl.
A61K 31/56 (2006.01)
A61P 11/06 (2006.01)
A61K 47/32 (2006.01)
A61K 9/00 (2006.01)

(52) U.S. Cl.
CPC ............. *A61K 47/32* (2013.01); *A61K 9/0078* (2013.01)

(58) Field of Classification Search
CPC ....... A61K 47/32; A61K 9/0078; A61K 31/56
See application file for complete search history.

(56) References Cited

U.S. PATENT DOCUMENTS

| | | | |
|---|---|---|---|
| 4,335,121 A | 6/1982 | Phillipps et al. | |
| 4,352,789 A | 10/1982 | Thiel | |
| 5,182,097 A | 1/1993 | Byron et al. | |
| 5,849,265 A | 12/1998 | Li-Bovet et al. | |
| 6,123,924 A * | 9/2000 | Mistry ................... | A61K 9/008 424/43 |
| 6,261,539 B1 | 7/2001 | Adjei et al. | |
| 6,787,532 B2 | 9/2004 | Biggadike et al. | |
| 7,521,068 B2 * | 4/2009 | Bosch et al. .................. | 424/489 |
| 7,759,328 B2 * | 7/2010 | Govind et al. ................ | 514/167 |
| 8,143,239 B2 * | 3/2012 | Govind et al. ................ | 514/167 |
| 2003/0032632 A1 * | 2/2003 | Crispps et al. ............... | 514/179 |
| 2004/0157815 A1 | 8/2004 | Cripps et al. | |
| 2006/0110335 A1 * | 5/2006 | Cajan et al. .................... | 424/47 |
| 2006/0216353 A1 | 9/2006 | Liversidge et al. | |
| 2007/0065374 A1 * | 3/2007 | Liversidge et al. ............ | 424/46 |

FOREIGN PATENT DOCUMENTS

| | | |
|---|---|---|
| CA | 2602341 | 9/2006 |
| CA | 2641883 | 8/2007 |
| EP | 0 372 777 | 6/1990 |
| EP | 0 513 127 | 1/1991 |
| EP | 0 536 235 | 6/1991 |
| EP | 0 518 601 | 6/1992 |
| EP | 0 616 525 | 12/1992 |
| EP | 0 605 578 | 7/1994 |
| EP | 0 616 523 | 9/1994 |
| EP | 0 918 507 | 6/1999 |
| EP | 0 920 302 | 6/1999 |
| EP | 1 248 597 | 12/2000 |
| WO | WO 93/05765 | 4/1993 |
| WO | WO 03/063843 A1 | 8/2003 |
| WO | WO 2004/069225 | 8/2004 |
| WO | WO 2005/055985 | 6/2005 |

OTHER PUBLICATIONS

European Pharmacopoeia, 5$^{th}$ ed., 2004, vol. 2, p. 2289.
International Search Report PCT/GB2008/050518 dated Jan. 22, 2009 (4 pgs.).

* cited by examiner

*Primary Examiner* — Mina Haghighatian
(74) *Attorney, Agent, or Firm* — Norton Rose Fulbright US LLP

(57) ABSTRACT

The present invention relates to pharmaceutical compositions and in particular to suspension aerosol pharmaceutical compositions, processes to obtain them and their use in inhalation therapy.

20 Claims, No Drawings

PHARMACEUTICAL AEROSOL COMPOSITIONS COMPRISING FLUTICASONE

CROSS-REFERENCE TO RELATED APPLICATION(S)

This application is a Section 371 National Stage Application of International No. PCT/GB2008/050518, filed 27 Jun. 2008 and published as WO 2009/001144 A2 on 31 Dec. 2008, which claims priority from the Great Britain Application 0712454.8, filed 27 Jun. 2007, the contents of which are incorporated herein in their entirety for all purposes.

FIELD OF THE INVENTION

The present invention relates to pharmaceutical compositions and in particular to suspension aerosol pharmaceutical compositions, processes to obtain them and their use in inhalation therapy.

BACKGROUND OF THE INVENTION

Drugs for treating respiratory and nasal disorders are frequently administered in aerosol compositions through the mouth or nose. One widely used method for dispensing such aerosol drug compositions involves making a suspension composition of the drug as a finely divided powder in a compressed liquefied gas known as a propellant. The suspension is stored in a sealed container capable of withstanding the pressure required to maintain the propellant as a liquid and the suspension is dispersed by activation of a dose metering valve affixed to the container.

A metering valve may be designed to consistently release a fixed, predetermined mass of the drug composition upon each activation. As the suspension is forced from the container through the dose metering valve by the vapour pressure of the propellant, the propellant rapidly vapourizes leaving a fast moving cloud of very fine particles of the drug composition. This cloud of particles is directed into the nose or mouth of the patient by a channeling device such as a cylinder or open ended cone.

Concurrently with the activation of the aerosol dose metering valve, the patient inhales the drug particles into the lungs or nasal cavity. Systems of dispensing drugs in this way are known as pressurised "metered dose inhalers" (MDIs).

The chemical species, S-fluoromethyl 6α,9α-difluoro-11β-hydroxy-16α-methyl-17-propionyloxy-3-oxoandrost-1,4-diene-17β-carbothioate is generically known as fluticasone propionate. Fluticasone propionate, first disclosed in U.S. Pat. No. 4,335,121, is a synthetic steroid of the glucocorticoid family. The related glucocorticoid, fluticasone furoate, S-fluoromethyl 6α,9α-difluoro-11β-hydroxy-16α-methyl-17-(2-furanylcarbonyl)oxy-3-oxoandrost-1,4-diene-17β-carbothioate, is disclosed in U.S. Pat. No. 6,787,532.

Glucocorticoid steroids have potent anti-inflammatory actions and are therefore useful in the treatment of a range of medical disorders and diseases. Fluticasone propionate is marketed for the treatment of asthma, allergic rhinitis, and skin disorders such as eczema, and fluticasone furoate is marketed for the treatment of allergic rhinitis. A combination product comprising fluticasone propionate and salmeterol xinafoate has also been approved for the treatment of asthma and chronic obstructive pulmonary disease (COPD).

Pressurized metered dose inhalers (MDIs) are widely used devices for the delivery of medicaments to the respiratory tract by inhalation via the oral and nasal routes. Though MDIs are used primarily for topical delivery of drugs to the respiratory tract for treatment of such diseases as asthma and chronic obstructive pulmonary disease (COPD), there is increasing interest in their use for systemic drug delivery. Classes of medicaments commonly delivered by MDIs include bronchodilators (e.g. beta-agonists and anti-cholinergics), corticosteroids, and anti-allergies.

MDI compositions are comprised of at least a medicament and a propellant, but the MDI compositions may further comprise one or more excipients other than propellant.

MDI compositions are generally characterized as either solutions or suspensions. A solution composition comprises the medicament dissolved or solubilized in propellant or in a mixture of propellant and one or more excipients. A suspension composition contains the medicament in the form of particles which are dispersed in the propellant or in a mixture of propellant and one or more other excipients.

Traditionally, the propellant system used in MDIs has consisted of one or more chlorofluorocarbons (CFCs), such as Freon 11 ($CCl_3F$), Freon 12 ($CCl_2F_2$), and Freon 114 ($CF_2ClCF_2Cl$). However, the CFC propellants are now believed to provoke the degradation of stratospheric ozone and thus their production and use are being phased out.

Hydrofluoroalkane (HFA) propellants, particularly 1,1,1,2-tetrafluoroethane (HFA-134a) and 1,1,1,2,3,3,3,-heptafluoropropane (HFA-227), are currently favoured as non-ozone depleting alternatives to the CFC propellants for respiratory drug delivery. Other alternatives to CFCs have been proposed, including dimethyl ether and low molecular weight hydrocarbons, such as propane and butane.

The efficiency of an aerosol device, such as an MDI, is a function of the dose deposited at the appropriate site in the respiratory tract. Deposition is affected by several factors, of which one of the most important is the aerodynamic particle size. The distribution of aerodynamic particle sizes of solid particles and/or droplets in an aerosol can be characterized by their mass median aerodynamic diameter (MMAD, the diameter around which the mass aerodynamic diameters are distributed equally) and geometric standard deviation (GSD, the measure of variability of the aerodynamic particle diameters). Aerosol particles of equivalent MMAD and GSD have similar deposition in the respiratory tract irrespective of their composition.

The aerodynamic particle size depends upon a number of factors, including temperature, pressure, primary drug particle size, metering volume, actuator spray orifice diameter, excipient particle size and concentration.

For inhalation therapy, there is a preference for aerosols in which particles for inhalation have an MMAD of about 0.5 to 100 μm, depending on the intended site of deposition. Particles smaller than 0.5 μm may be exhaled. Particles larger than 100 μm may clog the metering valve or actuator orifice and may undergo suboptimal deposition.

For inhalation therapy targeting the lungs, there is a preference for aerosols in which the particles for inhalation have an MMAD of about 0.5 to 10 μm, more preferably about 0.5 to 5 μm, and most preferably about 0.5 to 3 μm. Particles larger than about 5 μm in diameter are primarily deposited by inertial impaction in the oropharynx, particles of about 0.5 to 5 μm in diameter are ideal for deposition in the conducting airways, and particles of about 0.5 to 3 μm in diameter are desirable for aerosol delivery to the lung periphery.

For inhalation therapy targeting the nose, there is a preference for aerosols in which the particles for inhalation have an MMAD of about 5 to 100 µm, more preferably about 5 to 50 µm, and most preferably about 5 to 25 µm.

Numerous methods are known in the art for the preparation of suspension aerosol compositions for MDIs. The known methods generally comprise the mixing of pre-formed medicament powders, which are of a size suitable for inhalation therapy, with propellant and optionally one or more other excipients. Control of the particle size distribution of the aerosol particles generated from the suspension aerosol composition is accomplished primarily via control of the particle size distribution of the medicament powders used to prepare the composition. Thus, considerable care is normally taken to avoid dissolution of the medicament powder in the excipients, as any dissolution of the medicament powder during manufacture of the composition would result in loss of particle size control. Conventional methods for generating medicament powders suitable for preparation of compositions for inhalation therapy, such as suspension aerosol compositions for MDIs, include milling (micronization), spray drying, and supercritical fluid recrystallization.

Suspension aerosol compositions are known in the art and examples of such compositions are disclosed in WO 04/069225, EP 518601, U.S. Pat. No. 5,182,097, EP 616523, EP 616525, EP 918507, U.S. Pat. No. 6,261,539, EP 920302, EP 605578, EP 536235, EP 513127 and EP 1248597. However, the compositions exemplified in the prior have certain limitations particularly when attempting to formulate a composition comprising fluticasone propionate in propellant HFA-134a.

The conventional processes of MDI manufacture are generally characterized as either "pressure filling" or "cold filling". In pressure filling, the powdered medicament, optionally combined with one or more excipients, is placed in a suitable aerosol container capable of withstanding the vapour pressure of the propellant and fitted with a metering valve. The propellant is then forced as a liquid through the valve into the container. In an alternate process of pressure filling, the particulate drug is combined in a process vessel with propellant and optionally one or more excipients, and the resulting drug suspension is transferred through the metering valve fitted to a suitable MDI container. In cold filling, the powdered medicament, propellant which is chilled below its boiling point, and optionally one or more excipients are added to the MDI container, and a metering valve is fitted to the container. For both, pressure filling and cold filling processes, additional steps, such as mixing, sonication, and homogenization, are often advantageously included.

Patients often rely on medication delivered by MDIs for rapid treatment of respiratory disorders which are debilitating and in some cases even life threatening. Therefore, it is essential that each actuation and delivery of dose must be the same within very close limits. These dose limits of aerosol medication delivered to the patient must consistently meet the specifications claimed by the manufacturer and comply with the strict requirements of the regulatory authorities.

SUMMARY OF THE INVENTION

As described above, consistent delivery of dose is essential for safety and efficacy of an aerosol pharmaceutical composition. Surprisingly, it has been found by the current inventors that certain polymers are capable of stabilizing fluticasone aerosol compositions so that dosing is obtained with consistent MMAD and GSD. The compositions of the invention are also very stable and have a long shelf life which is also essential for gaining regulatory approval for market.

Thus, according to a first aspect of the invention, there is provided an aerosol pharmaceutical composition comprising fluticasone or a pharmaceutically acceptable derivative thereof, a propellant and a stabilizing polymer.

A second aspect of the invention provides a process for the preparation of a composition according to the first aspect of the invention, which comprises dispersing (including dissolving and suspending, preferably suspending) the fluticasone or the pharmaceutically acceptable derivative thereof and the stabilizing polymer in the propellant.

A third aspect of the invention provides the use of a composition according to the first aspect of the invention in the preparation of a medicament for the treatment of respiratory disorders, such as asthma, emphysema, respiratory distress syndrome, chronic obstructive pulmonary disease (COPD), chronic bronchitis, cystic fibrosis, and AIDS related respiratory disorders including AIDS related pneumonia. Particularly preferred is the preparation of a medicament for the treatment of inflammatory respiratory disorders such as asthma or COPD.

A fourth aspect of the invention provides the use of PVP in an aerosol pharmaceutical composition with fluticasone propionate and propellant to give optimum performance without the requirement for other excipients.

A fifth aspect of the invention provides a composition for use in a pharmaceutical aerosol, comprising a propellant and a stabilizing polymer. Thus, the fifth aspect of the invention provides a pharmaceutical aerosol composition according to the first aspect of the invention, but without the fluticasone or pharmaceutically acceptable derivative thereof.

One embodiment of the second aspect of the invention comprises dispersing (including dissolving and suspending, preferably suspending) fluticasone or a pharmaceutically acceptable derivative thereof in a composition according to the fifth aspect of the invention.

The composition according to the first aspect of the invention may be used in an oral MDI device or a nasal spray. Thus a sixth aspect of the invention provides an aerosol canister, such as an MDI or nasal spray, comprising an aerosol pharmaceutical composition according to the first aspect of the invention.

In all aspects of the invention, preferably the fluticasone is present in the form of fluticasone propionate or fluticasone furoate.

The stabilizing polymer may be a homopolymer, that is the polymer consists of the same recurring structural units, or it may be a co-polymer, that is the polymer contains recurring units that are not the same.

Preferred stabilizing polymers include recurring structural units containing an amide group.

In general, it has been found that polyvinylpyrrolidones having a wide range of average molecular weights give excellent aerosol pharmaceutical compositions, in particular suspensions. Particularly preferred embodiments of the invention are when the stabilizing polymer is polyvinylpyrrolidone (PVP), also known as povidone. Different types of PVP may be characterized by their viscosity in solution, expressed as a K-value (see European Pharmacopoeia, 5$^{th}$ ed., 2004, vol. 2, page 2289). Preferably the K-value of the PVP used is between 10 and 150, more preferably between 15 and 80, more preferably between 20 and 40, most preferably about 30. Suitable polyvinylpyrrolidones are PVP (K30), Povidone K30, PVP(K29/32), PVP(K90), PVP (K120), PVP(C15), PVP(C30) or PVP/17PF.

Alternatively, the stabilizing polymer is a PEG derivative or a co-polymer of vinyl acetate and vinyl pyrrolidone.

As used herein, a PEG derivative is a compound comprising one or more —(CH$_2$CH$_2$O)$_n$— recurring units, wherein n is an integer ≥2. Preferably n is ≥4, ≥6 or ≥8. In one embodiment, n is ≤20. Preferred PEG derivatives are linear. Most preferably the PEG derivative is polyethylene glycol (PEG), i.e. HO—(CH$_2$CH$_2$O)$_n$—H. Preferably the average molecular weight of the PEG or PEG derivative is 50 to 1000 Da, more preferably 100 to 500 Da, most preferably 200 to 400 Da. Preferred PEGs include PEG 200 and PEG 400.

Alternative stabilizing polymers also include those containing carboxylic acid ester containing recurring structural units such as polyvinyl acetate and co-polymers of vinyl acetate and vinyl pyrrolidone, e.g. polyvinylpyrrolidone/vinyl acetate co-polymer.

In one embodiment of the present invention, the aerosol pharmaceutical composition comprises fluticasone or a pharmaceutically acceptable derivative thereof, HFA-134a and polyvinylpyrrolidone, wherein said composition contains no alcoholic co-solvent. Preferably said composition contains no polar protic co-solvent, more preferably said composition contains no polar co-solvent. Preferably said composition contains only fluticasone or a pharmaceutically acceptable derivative thereof, HFA-134a and polyvinylpyrrolidone; and optionally one or more other pharmacologically active agents.

In another embodiment of the present invention, the aerosol pharmaceutical composition comprises fluticasone or a pharmaceutically acceptable derivative thereof, a hydrofluoroalkane and a PEG derivative. In one embodiment said composition contains no alcoholic co-solvent, preferably no polar protic co-solvent, more preferably no polar co-solvent. Preferably said composition contains only fluticasone or a pharmaceutically acceptable derivative thereof, a hydrofluoroalkane and a PEG derivative; and optionally one or more other pharmacologically active agents. Alternatively, preferably said composition contains only fluticasone or a pharmaceutically acceptable derivative thereof, a hydrofluoroalkanes, a PEG derivative and a polar co-solvent; and optionally one or more other pharmacologically active agents.

The amount of stabilizing polymer in the composition will depend on the active ingredient to be dispersed, the concentration of the active ingredient and the particular polymer selected. However, in general the amount of stabilizing polymer is from 0.00001 to 10% w/w, more preferably 0.0001 to 5% w/w and especially 0.001 to 1% w/w.

The stabilizing polymer may be present in the composition in solution or in suspension. Preferably the stabilizing polymer is present in the composition in suspension. Preferably at least 10%, 20%, 30%, 40%, 50%, 60%, 70%, 80%, 90%, or 95% of the stabilizing polymer is not dissolved in the propellant, i.e. preferably at least 10%, 20%, 30%, 40%, 50%, 60%, 70%, 80%, 90%, or 95% of the stabilizing polymer is present as suspended particles in the propellant. It has been found that when the stabilizing polymer is present in the composition in suspension surprisingly superior results in the performance characteristic tests (as described below) are observed.

The term "propellant" as used herein means one or more pharmacologically inert liquids or gases which exert a vapour pressure at room temperature sufficient to propel the medicament from the container to the patient on actuation of the metering valve. Preferably, the propellant will be a weak solvent or a non-solvent for the medicament; most preferably, the propellant will be a non-solvent for the medicament. Suitable propellants include, for example, hydrofluoroalkanes such as 1,1,1,2-tetrafluoroethane (CF$_3$CH$_2$F) (HFA-134a) and 1,1,1,2,3,3,3-heptafluoropropane (CF$_3$CHFCF$_3$) (HFA-227), perfluoroethane, monochloro-difluoromethane, 1,1-difluoroethane (HFA-152a), tetrafluoromethane (PFC-14), trifluoromethane (HFA-23), difluoromethane (HFA-32), fluoromethane (HFA-41), 1,1,2,2,2-pentafluoroethane (HFA-125), 1,1,2,2-tetrafluoroethane (HFA-134), decafluorobutane (CF$_3$CF$_2$CF$_2$CF$_3$); dialkyl ethers such as dimethyl ether; and low molecular weight hydrocarbons such as n-butane, iso-butane, and propane. Propellants may be used singly or in combination. Preferably, the propellant is in a substantially liquid state as it is mixed with the medicament. The propellant may be used in a non-supercritical state.

Preferably the propellant used in the invention is HFA-227 or HFA-134a or mixtures thereof, but most preferably it is HFA-134a. It was found that use of HFA-134a as the propellant and PVP as the stabilizing polymer gave surprisingly effective and synergistic results with respect to the performance of the compositions.

Typically, the PVP is present in the composition at a concentration of between 0.001% to 5% by weight, preferably between 0.001% to 1% by weight, and most preferably between 0.001% to 0.1% by weight.

The term "fluticasone or a pharmaceutically acceptable derivative thereof" includes compounds of the formula (I):

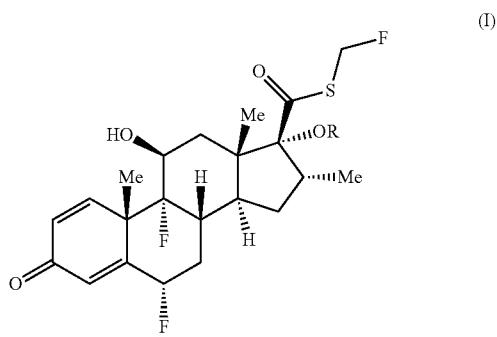

and pharmaceutically acceptable salts, solvates and hydrates thereof, wherein R is hydrogen or —COR$^x$, and wherein R$^x$ is an optionally substituted alkyl, alkenyl, alkynyl, aryl or heteroaryl group, preferably comprising up to 10 carbon atoms. An optionally substituted alkyl, alkenyl, alkynyl, aryl or heteroaryl group may be substituted with one or more of —F, —Cl, —Br, —I, —CF$_3$, —CCl$_3$, —CBr$_3$, —CI$_3$, —OH, —SH, —NH$_2$, —CN, —NO$_2$, —COOH, —OR', —SR', —N(R')$_2$, —COR', —CO$_2$R', —O—COR', —CON(R')$_2$, or —R', wherein —R' is independently hydrogen, unsubstituted C$_1$-C$_6$ alkyl or unsubstituted C$_6$-C$_{10}$ aryl. Preferably R$^x$ is ethyl or 2-furanyl.

For the purposes of this invention, a "salt" of a compound of the present invention may be an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid). The acid addition salt may be a mono- or di-acid addition salt. A preferred salt is a hydrohalogenic, sulphuric, phosphoric or organic acid addition salt.

For the purposes of this invention, a "salt" of a compound of the present invention may also be formed between an acidic functionality of a compound of the present invention and a suitable cation. Suitable cations include, but are not limited to lithium, sodium, potassium, magnesium, calcium and ammonium. The salt may be a mono- or di-salt. Preferably the salt is a mono- or di-lithium, sodium, potassium, magnesium, calcium or ammonium salt. More preferably the salt is a mono-sodium salt. Preferably the salt is a pharmaceutically acceptable salt.

Ideally the fluticasone or the pharmaceutically acceptable derivative thereof is present in the composition at a concentration of between 0.05% to 5% by weight, preferably between 0.05% to 1% by weight, and most preferably between 0.01% to 0.1% by weight.

The fluticasone or the pharmaceutically acceptable derivative thereof may be present in the composition in solution or in suspension. Preferably the fluticasone or pharmaceutically acceptable derivative thereof is present in the composition in suspension. Preferably at least 80%, 90%, 95%, 98%, 99%, or 99.9% of the fluticasone or the pharmaceutically acceptable derivative thereof is not dissolved in the propellant, i.e. preferably at least 80%, 90%, 95%, 98%, 99%, or 99.9% of the fluticasone or the pharmaceutically acceptable derivative thereof is present as suspended particles in the propellant.

The term "excipients" as used herein means chemical agents having little or no pharmacological activity (for the quantities used), but which enhance the drug composition or the performance of the MDI system. For example, excipients include but are not limited to surfactants, preservatives, flavourings, anti-oxidants, anti-aggregating agents, and co-solvents, e.g. ethanol.

Therefore, the compositions of the invention may, in addition to the stabilizing polymer, contain other excipients, in particular excipients intended to improve valve lubrication and excipients to modify flavour. Particular lubricants that may be mentioned include polysorbates, e.g. polysorbate 80, and alkyl aryl polyether alcohols, e.g. tyloxapol. Other lubricating excipients that may be employed include high molecular weight fully halogenated chlorofluorocarbons and esters of medium chain fatty acids. The amount of lubricant in the composition will depend on the other components of the composition, the active ingredient, the nature of the valve, etc. In general, a concentration of 0.01 to 4% w/w and more preferably 0.1 to 2% w/w of lubricant is preferred.

Surfactants are commonly added to aerosol compositions in particular solutions, for example to lubricate the valve components in the inhaler device and/or improve the physical stability of the aerosol compositions. Suitable surfactants include both non-fluorinated surfactants and fluorinated surfactants known in the art and disclosed, for example, in U.S. Pat. Nos. 5,849,265 and 4,352,789. Examples of suitable surfactants which can be used in the compositions in addition to the stabilizing polymer include oleic acid; lecithins from synthetic and natural sources; sorbitan trioleate; sorbitan mono-oleate; sorbitan monolaurate; tetrahydrofurfuryl oleate; ethyl oleate; isopropyl myristate; glyceryl trioleate; glyceryl mono-oleate; glyceryl monolaurate; glyceryl monostearate; glyceryl monoricinoleate; cetyl alcohol; stearyl alcohol; and cetyl pyridinium chloride. Preferred surfactants are oleic acid, lecithin, and sorbitan trioleate.

In one embodiment of the present invention, the aerosol pharmaceutical composition contains only fluticasone or a pharmaceutically acceptable derivative thereof, a propellant, a stabilizing polymer and a surfactant; and optionally one or more other pharmacologically active agents.

Surfactants, if used, are generally present in amounts not exceeding 5% by weight of the total composition, though higher amounts may be used. They will usually be present in the weight ratio 1:100 to 10:1 surfactant:medicament(s), but higher or lower surfactant:medicament(s) ratios may be employed.

The amount of optional surfactant employed is desirably in the range of 0.0001% to 5% weight to weight ratio relative to the drug, preferably 0.05 to 5% weight to weight ratio.

It should be noted that the stabilizing polymer present in the compositions of the invention can also act as a surfactant and/or a lubricant. It has been surprisingly found that PVP can be used in the aerosol pharmaceutical composition with fluticasone propionate and propellant (e.g. HFA-134a) to give optimum performance without the requirement for other excipients.

Flavour modifying excipients that may be added to the composition include peppermint oil, menthol, saccharin and saccharin sodium. When the flavour modifying excipient is a solid, preferably it is micronized. The concentration will depend on the individual composition and the flavour modifying excipient. Typically, a concentration of 0.005 to 4% w/w, and more preferably 0.01 to 1% w/w is used.

A polar co-solvent, preferably a polar protic co-solvent such as aliphatic alcohols and polyols, e.g. ethanol, isopropanol and propylene glycol, may be included in the composition. Preferably said polar co-solvent contains 1-6 carbon atoms, more preferably 1-4 carbon atoms, most preferably 1-3 carbon atoms. A preferred co-solvent is ethanol and typically, the aerosol composition may contain 0.01 to 5% w/w of the co-solvent, preferably 0.1 to 5% w/w, and most preferably 0.1 to 1% w/w. For suspension compositions the amount of these polar co-solvents must be controlled so as not to dissolve the active ingredient and/or the stabilizing polymer to any significant extent.

It will be appreciated by those skilled in the art that the aerosol composition for use in the invention may, if desired, contain fluticasone or a pharmaceutically acceptable derivative thereof, e.g. fluticasone in the form of a suitable ester such as the propionate or the furoate ester (or a physiologically acceptable solvate or hydrate thereof), optionally in combination with one or more other pharmacologically active agents. Such medicaments may be selected from any suitable drug useful in inhalation therapy. Appropriate medicaments may thus be selected from, for example, analgesics, e.g. codeine, dihydromorphine, ergotamine, fentanyl or morphine; anginal preparations, e.g. diltiazem; anti-allergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone (e.g. the dipropionate), flunisolide, budesonide, tipredane or triamcinolone acetonide; anti-tussives, e.g. noscapine; bronchodilators, e.g. salbutamol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or orciprenaline; diuretics, e.g. amiloride; anti-cholinergics, e.g. ipratropium, atropine or oxitropium; hormones, e.g. cortisone, hydrocortisone or prednisolone; xanthines, e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Said other pharmacologically active agents may be present in the composition in solution or in suspension. Preferably said other pharmacologically active agents are present in the composition in suspension.

Particularly preferred combination compositions contain fluticasone or a pharmaceutically acceptable derivative thereof, such as fluticasone propionate (or a physiologically acceptable solvate or hydrate thereof), in combination with a bronchodilator such as salbutamol (e.g. as the free base or the sulphate salt) or salmeterol (e.g. as the xinafoate salt) or formoterol (e.g. as the fumarate salt). A particularly preferred combination is fluticasone propionate and salmeterol xinafoate. Another particularly preferred combination is fluticasone propionate and formoterol fumarate.

In general the vapour pressure of the propellant mixture should be in a range suitable and permitted for aerosol propellants. The vapour pressure of the compositions of the invention may be varied by mixing one or more propellants and/or some other suitable vapour pressure modifying agent in appropriate proportions.

In particular, the compositions may be produced by cold fill or pressure fill techniques. In cold filling, the ingredients are placed in a cooled mixing vessel, cooled liquefied propellant is added and a dispersion is produced by vigorous stirring. Alternatively, a slurry may be prepared of the ingredients in a portion of cooled liquefied propellant and the remainder of the liquefied propellant added under vigorous stirring. Aliquots of the dispersed composition are then filled into cooled aerosol cans and sealed with a suitable valve, e.g. a metering valve.

In pressure filling, the ingredients are placed in a pressure vessel, liquefied propellant is added under pressure through a valve, and a dispersion of the ingredients in the liquefied propellant is then filled, under pressure, through the valve into suitable cans provided with appropriate valves, e.g. metering valves.

The compositions according to the invention are advantageous in that the stabilizing polymer may ensure good dispersion of the medicament and smooth operation of the aerosol valve.

The performance of the compositions according to the present invention can be assessed using test procedures which are well known to those skilled in the art. Suitable test procedures include: settling times, dispersion tests, lubrication, dose uniformity, caking potential and stability tests.

The term "aerosol pharmaceutical composition" as used herein refers to a composition suitable for inhalation therapy, for example an MDI composition, wherein at least one medicament is preferably in the form of fine particles which are substantially insoluble in the composition. The term "fine particles" as used herein refers to medicament particles with an MMAD suitable for use in inhalation therapy. Fine particles may exist, for example, in dry powder form, in suspension in a fluid, or within an aerosol.

Preferably the aerosol particles generated from the aerosol pharmaceutical compositions of the present invention have an MMAD of about 0.5 to 100 μm, preferably about 0.5 to 10 μm, more preferably about 0.5 to 5 μm, and most preferably about 0.5 to 3 μm.

Aerosol compositions prepared according to the present invention may be filled into or formed in aerosol canisters suitable for delivering pharmaceutical aerosol compositions. Aerosol canisters generally comprise a container or reservoir capable of withstanding the vapour pressure of the propellant used, such as a plastic bottle, a plastic-coated glass bottle, or a metal can, such as an aluminium can which may optionally be anodized, lacquer-coated and/or plastic-coated (e.g. fluoropolymer-coated).

The aerosol canister may be fitted with a metering valve capable of delivering a measured dose of the aerosol composition in the form of an aerosol. Suitable valves are commercially available from manufacturers well known in the aerosol industry, for example from Bespak (e.g. BK356), Valois (e.g. DF10), and 3M-Neotechnic Ltd. (e.g. Spraymiser). The propellant may be added to the canister through the metering valve, or the propellant may be added to the canister prior to sealing the canister with the metering valve. Prior to use, each aerosol canister is fitted into a suitable actuator for dispensing the medicament from the metering valve to the patient.

The following paragraphs enumerated consecutively from 1 through 36 provide for various aspects of the present invention. In one embodiment, the present invention provides:

1. An aerosol pharmaceutical composition comprising fluticasone or a pharmaceutically acceptable derivative thereof, a propellant and a stabilizing polymer.
2. A composition according to paragraph 1, wherein the stabilizing polymer is polyvinylpyrrolidone (PVP).
3. A composition according to paragraph 2, wherein the PVP is povidone K30.
4. A composition according to paragraph 1, wherein the stabilizing polymer is a PEG derivative.
5. A composition according to paragraph 1, wherein the stabilizing polymer is a co-polymer of vinyl acetate and vinyl pyrrolidone.
6. A composition according to any one of the preceding paragraphs, wherein the concentration of polymer is from 0.00001 to 10% w/w.
7. A composition according to any one of paragraphs 1 to 6, wherein the propellant is HFA-134a.
8. A composition according to any one of paragraphs 1 to 6, wherein the propellant is HFA-227.
9. A composition according to any one of the preceding paragraphs, comprising fluticasone propionate.
10. A composition according to any one of the preceding paragraphs, comprising fluticasone furoate.
11. A composition according to paragraph 1, comprising 0.05 to 5% w/w fluticasone or a pharmaceutically acceptable derivative thereof and 0.001 to 5% w/w of a stabilizing polymer.
12. A composition according to paragraph 1, comprising 0.05 to 0.5% w/w fluticasone propionate and 0.001 to 0.1% w/w polyvinylpyrrolidone, with the remainder being HFA-134a.
13. A composition according to paragraph 1, comprising about:

| Fluticasone Propionate | 8.50 mg (0.081%) |
|---|---|
| Povidone K30 (PVP) | 1.69 mg (0.016%) |
| HFA-134a | 10.5298 g (99.903%) |

14. A composition according to paragraph 1, comprising about:

| Fluticasone Propionate | 18.75 mg (0.149%) |
|---|---|
| Povidone K30 (PVP) | 2.02 mg (0.016%) |
| HFA-134a | 12.57923 g (99.835%) |

15. A composition according to paragraph 1, comprising about:

| Fluticasone Propionate | 37.55 mg (0.298%) |
|---|---|
| Povidone K30 (PVP) | 2.02 mg (0.016%) |
| HFA-134a | 12.5604 g (99.686%) |

16. A process for the preparation of a composition according to any one of the preceding paragraphs, which comprises dispersing the fluticasone or the pharmaceutically derivative thereof and the stabilizing polymer in the propellant.

17. A process according to paragraph 16, wherein the stabilizing polymer is polyvinylpyrrolidone (PVP).

18. A process according to paragraph 17, wherein the PVP is povidone K30.

19. A process according to paragraph 16, wherein the stabilizing polymer is a PEG derivative.

20. A process according to paragraph 16, wherein the stabilizing polymer is a co-polymer of vinyl acetate and vinyl pyrrolidone.

21. A process according to any one of paragraphs 16 to 20, wherein the concentration of polymer is from 0.00001 to 10% w/w.

22. A process according to any one of paragraphs 16 to 21, wherein the propellant is HFA-134a.

23. A process according to any one of paragraphs 16 to 21, wherein the propellant is HFA-227.

24. A process according to any one of paragraphs 16 to 23, comprising fluticasone propionate.

25. A process according to any one of paragraphs 16 to 23, comprising fluticasone furoate.

26. Use of a composition according to any one of paragraphs 1 to 15, in the preparation of a medicament for the treatment of a respiratory disorder.

27. The use according to paragraph 26, wherein the respiratory disorder is asthma, emphysema, respiratory distress syndrome, chronic obstructive pulmonary disease (COPD), chronic bronchitis, cystic fibrosis, an AIDS related respiratory disorder, or AIDS related pneumonia.

28. The use according to paragraph 27, wherein the respiratory disorder is asthma.

29. The use according to paragraph 27, wherein the respiratory disorder is COPD.

30. Use of PVP in an aerosol pharmaceutical composition comprising fluticasone propionate and a propellant, wherein the use of PVP improves the performance of the aerosol pharmaceutical composition.

31. The use according to paragraph 30, wherein the use of PVP gives optimum performance without the requirement for other excipients.

32. The use according to paragraph 30 or 31, wherein the propellant is HFA-134a.

33. The use according to any one of paragraphs 30 to 32, wherein the PVP is povidone K30.

34. A composition for use in a pharmaceutical aerosol, comprising a propellant and a stabilizing polymer.

35. A process according to any one of paragraphs 16 to 25, comprising dispersing fluticasone or a pharmaceutically acceptable derivative thereof in a composition according to paragraph 34.

36. An aerosol canister comprising an aerosol pharmaceutical composition according to any one of paragraphs 1 to 15.

The following examples are provided to illustrate the present invention and should not be construed as limiting thereof.

EXAMPLES

The following compositions were prepared using standard methods well known to those skilled in the art. The compositions were filled into aluminium aerosol canisters having a fluoropolymer coating comprising either an ethylenetetrafluoroethylene co-polymer (ETFE) or a blend of perfluorinated ethylene propylene co-polymer (FEP) and polyethersulphone (PES). Aerosol canisters were fitted with metering valves obtained from Bespak. As observed visually in glass bottles, compositions prepared according to the present invention were in the form of suspensions which were readily dispersed by hand shaking. The suspension stability was suitable for use with a metered dose inhaler.

Particle size distributions of the aerosol particles generated from the suspension aerosol compositions were determined using an 8-stage Andersen cascade impactor (ACI). MMAD and GSD were calculated from the ACI data as prescribed by the European Pharmacopoeia ($5^{th}$ ed., 2004). ACI testing was performed using a Bespak actuator having an orifice diameter of 0.48 mm. The compositions in the examples were designed to deliver 50 μg/dose, 125 μg/dose or 250 μg/dose per actuation.

Example 1

| Fluticasone Propionate | 8.50 mg (0.081%) |
|---|---|
| Povidone K30 (PVP) | 1.69 mg (0.016%) |
| HFA-134a | 10.5298 g (99.903%) |

Example 2

| Fluticasone Propionate | 18.75 mg (0.149%) |
|---|---|
| Povidone K30 (PVP) | 2.02 mg (0.016%) |
| HFA-134a | 12.57923 g (99.835%) |

Example 3

| Fluticasone Propionate | 37.55 mg (0.298%) |
|---|---|
| Povidone K30 (PVP) | 2.02 mg (0.016%) |
| HFA-134a | 12.5604 g (99.686%) |

Example 4

| Fluticasone Propionate | 8.50 mg (0.081%) |
|---|---|
| Povidone K30 (PVP) | 1.69 mg (0.016%) |
| HFA-227 | 10.5298 g (99.903%) |

Example 5

| Fluticasone Propionate | 18.75 mg (0.149%) |
|---|---|
| Povidone K30 (PVP) | 2.02 mg (0.016%) |
| HFA-227 | 12.57923 g (99.835%) |

Example 6

| Fluticasone Propionate | 37.55 mg (0.298%) |
|---|---|
| Povidone K30 (PVP) | 2.02 mg (0.016%) |
| HFA-227 | 12.5604 g (99.686%) |

Example 7

| Fluticasone Propionate | 8.50 mg (0.081%) |
|---|---|
| PEG 400 | 0.85 mg (0.008%) |
| Oleic acid | 0.85 mg (0.008%) |
| HFA-134a | 10.5298 g (99.903%) |

Example 8

| Fluticasone Propionate | 18.75 mg (0.149%) |
|---|---|
| Povidone K30 (PVP) | 1.01 mg (0.008%) |
| Oleic Acid | 1.01 mg (0.008%) |
| HFA-134a | 12.57923 g (99.835%) |

Example 9

| Fluticasone Propionate | 37.55 mg (0.298%) |
|---|---|
| Povidone K30 (PVP) | 1.01 mg (0.008%) |
| Oleic Acid | 1.01 mg (0.008%) |
| HFA-134a | 12.5604 g (99.686%) |

The performance of the compositions according to examples 1-9 was assessed using standard test procedures known to the person skilled in the art. All example compositions gave generally satisfactory performance with respect to the following performance characteristic tests: settling times, dispersion tests, lubrication, dose uniformity, caking potential and stability tests.

However it was found that examples 1, 2 and 3, comprising fluticasone propionate in HFA-134a, gave very superior results in the performance characteristic tests (e.g. settling times, dispersion tests, lubrication, dose uniformity, caking potential and stability tests), and surprisingly effective and synergistic results with respect to the performance characteristics and stability with no requirement for the inclusion of excipients such as lubricants, surfactants and/or co-solvents, in addition to PVP. In particular, the compositions according to examples 1, 2 and 3 gave very superior results in respect of dose uniformity over the life of the aerosol canisters and in respect of dose uniformity over time. Therefore very simple formulations comprising only active ingredient, propellant and one excipient have been developed.

What is claimed is:

1. An aerosol canister containing an aerosol pharmaceutical composition, wherein the aerosol pharmaceutical composition comprises fluticasone or a pharmaceutically acceptable derivative thereof, 1,1,1,2-tetrafluoroethane and polyvinylpyrrolidone (PVP), wherein the polyvinylpyrrolidone is present as suspended particles in the 1,1,1,2-tetrafluoroethane.

2. An aerosol canister according to claim 1:
   (i) wherein the polyvinylpyrrolidone is povidone K30; and/or
   (ii) wherein the concentration of the polyvinylpyrrolidone in the composition is from 0.00001 to 10% w/w; and/or
   (iii) wherein the aerosol pharmaceutical composition comprises fluticasone propionate; and/or
   (iv) wherein the aerosol pharmaceutical composition comprises fluticasone furoate; and/or
   (v) wherein the concentration of the fluticasone or the pharmaceutically acceptable derivative thereof in the composition is from 0.05 to 5% w/w and the concentration of the polyvinylpyrrolidone in the composition is from 0.001 to 5% w/w; and/or
   (vi) wherein the aerosol pharmaceutical composition comprises fluticasone propionate, wherein the concentration of the fluticasone propionate in the composition is from 0.05 to 0.5% w/w and the concentration of the polyvinylpyrrolidone in the composition is from 0.001 to 0.1% w/w, with the remainder being 1,1,1,2-tetrafluoroethane.

3. An aerosol canister according to claim 2, wherein the aerosol pharmaceutical composition comprises:

| fluticasone propionate | about 8.50 mg (0.081%) |
|---|---|
| povidone K30 (PVP) | about 1.69 mg (0.016%) |
| 1,1,1,2-tetrafluoroethane | about 10.5298 g (99.903%). |

4. An aerosol canister according to claim 2, wherein the aerosol pharmaceutical composition comprises:

| fluticasone propionate | about 18.75 mg (0.149%) |
|---|---|
| povidone K30 (PVP) | about 2.02 mg (0.016%) |
| 1,1,1,2-tetrafluoroethane | about 12.57923 g (99.835%). |

5. An aerosol canister according to claim 2, wherein the aerosol pharmaceutical composition comprises:

| fluticasone propionate | about 37.55 mg (0.298%) |
|---|---|
| povidone K30 (PVP) | about 2.02 mg (0.016%) |
| 1,1,1,2-tetrafluoroethane | about 12.5604 g (99.686%). |

6. A process for the preparation of an aerosol canister according to claim 1, which comprises dispersing the fluticasone or the pharmaceutically derivative thereof and the polyvinylpyrrolidone in the 1,1,1,2-tetrafluoroethane.

7. A process according to claim 6:
   (i) wherein the polyvinylpyrrolidone is povidone K30; and/or
   (ii) wherein the concentration of the polyvinylpyrrolidone in the composition is from 0.0001 to 10% w/w; and/or
   (iii) wherein the aerosol pharmaceutical composition comprises fluticasone propionate; and/or
   (iv) wherein the aerosol pharmaceutical composition comprises fluticasone furoate.

8. A method of treating a respiratory disorder, the method comprising administering a therapeutically effective amount of a composition from an aerosol canister according to claim 1 to a patient in need thereof, wherein:
- (i) the respiratory disorder is selected from the group consisting of asthma, emphysema, respiratory distress syndrome, chronic obstructive pulmonary disease (COPD), chronic bronchitis, cystic fibrosis, an AIDS related respiratory disorder, and AIDS related pneumonia; or
- (ii) the respiratory disorder is selected from the group consisting of asthma and COPD.

9. An aerosol canister according to claim 1, wherein the composition does not include other excipients.

10. A process according to claim 6, comprising dispersing the fluticasone or a pharmaceutically acceptable derivative thereof in a composition comprising the 1,1,1,2-tetrafluoroethane and the polyvinylpyrrolidone.

11. An aerosol canister according to claim 1, wherein the composition contains no alcoholic co-solvent.

12. An aerosol canister according to claim 1, wherein:
- (i) at least 20% of the polyvinylpyrrolidone is not dissolved in the 1,1,1,2-tetrafluoroethane; or
- (ii) at least 40% of the polyvinylpyrrolidone is not dissolved in the 1,1,1,2-tetrafluoroethane; or
- (iii) at least 60% of the polyvinylpyrrolidone is not dissolved in the 1,1,1,2-tetrafluoroethane; or
- (iv) at least 80% of the polyvinylpyrrolidone is not dissolved in the 1,1,1,2-tetrafluoroethane.

13. An aerosol canister according to claim 1, wherein the aerosol particles generated from the composition have a mass median aerodynamic diameter (MMAD) of about 0.5 to 100 μm.

14. An aerosol canister according to claim 1, wherein the composition contains no polar protic co-solvent.

15. An aerosol canister according to claim 1, wherein the composition contains no polar co-solvent.

16. An aerosol canister according to claim 1, wherein the fluticasone or the pharmaceutically acceptable derivative thereof is suspended in the composition.

17. An aerosol canister according to claim 1, wherein the concentration of the fluticasone or the pharmaceutically acceptable derivative thereof in the composition is from 0.05 to 1% w/w.

18. An aerosol canister according to claim 1, wherein the K-value of the polyvinylpyrrolidone is between 20 and 40.

19. An aerosol canister according to claim 1, wherein the concentration of the polyvinylpyrrolidone in the composition is from 0.001 to 0.1% w/w.

20. An aerosol canister according to claim 1, wherein composition contains only fluticasone or a pharmaceutically acceptable derivative thereof, 1,1,1,2-tetrafluoroethane and polyvinylpyrrolidone.

* * * * *